US012678452B2

(12) United States Patent     (10) Patent No.:   US 12,678,452 B2

Pene et al.     (45) Date of Patent:     Jul. 14, 2026

(54) ORAL COMPOSITION FOR PERIMENOPAUSE

(71) Applicant: HuntGreenLiving LLC, New York, NY (US)

(72) Inventors: Marina Pene, Brooklyn, NY (US); Eunjung Kim, New York, NY (US); Vera Martins, London (GB)

(73) Assignee: HUNTGREENLIVING LLC, New York, NY (US)

( * ) Notice: Subject to any disclaimer, the term of this patent is extended or adjusted under 35 U.S.C. 154(b) by 578 days.

(21) Appl. No.: 18/311,770

(22) Filed: May 3, 2023

(65) Prior Publication Data

US 2024/0041905 A1     Feb. 8, 2024

Related U.S. Application Data

(60) Provisional application No. 63/396,124, filed on Aug. 8, 2022.

(51) Int. Cl.

| | |
|---|---|
| *A61K 31/00* | (2006.01) |
| *A23L 33/105* | (2016.01) |
| *A61K 36/31* | (2006.01) |
| *A61K 36/54* | (2006.01) |
| *A61K 36/79* | (2006.01) |
| *A61K 36/81* | (2006.01) |
| *A61K 36/9066* | (2006.01) |
| *A61P 15/12* | (2006.01) |

(52) U.S. Cl.

CPC ............ *A61K 31/658* (2023.05); *A61K 36/31* (2013.01); *A61K 36/54* (2013.01); *A61K 36/79* (2013.01); *A61K 36/81* (2013.01); *A61K 36/9066* (2013.01); *A61P 15/12* (2018.01); *A23L 33/105* (2016.08)

(58) Field of Classification Search

None

See application file for complete search history.

(56) References Cited

U.S. PATENT DOCUMENTS

| | | | |
|---|---|---|---|
| 2020/0197356 A1* | 6/2020 | Firger | A61K 33/04 |
| 2020/0330536 A1 | 10/2020 | Velazquez et al. | |
| 2021/0401736 A1* | 12/2021 | Wan | A61K 31/658 |
| 2022/0071984 A1* | 3/2022 | Poole | A61K 9/006 |

FOREIGN PATENT DOCUMENTS

| | | |
|---|---|---|
| GB | 2623163 | 4/2024 |
| KR | 101822834 | 1/2018 |
| RO | 127627 | 6/2013 |

OTHER PUBLICATIONS

Rezazadeh, K., et al., Antioxidant response to artichoke leaf extract supplementation in metabolic syndrome: A double-blind placebo-controlled randomized clinical trial, Clinical Nutrition, vol. 37, Jun. 2018, 790-796 (Year: 2018).*

Honma, A., et al., The improvement of daily fatigue in women following the intake of maca (*Lepidium meyenii*) extract containing benzyl glucosinolate. Functional Foods in Health and Disease. 2022;12(4): 175-187 (Year: 2022).*

UK Patent Application 2312074.4 Search Report mailed on Feb. 5, 2024.

* cited by examiner

*Primary Examiner* — H. Sarah Park

(74) *Attorney, Agent, or Firm* — KNH LLP

(57) ABSTRACT

Compositions and methods are disclosed for treating one or more symptoms of perimenopause. A composition includes a cannabidiol, a *Curcuma longa* extract, and/or a *Lepidium meyenii* extract. A method of manufacturing a composition comprises including a cannabidiol, a *Curcuma longa* extract, and/or a *Lepidium meyenii* extract in the composition. A method of administering a composition includes administering a cannabidiol, a *Curcuma longa* extract, and/or a *Lepidium meyenii* extract of the composition.

13 Claims, 9 Drawing Sheets

300

110

120

202 204 206 302 304 306 308 310 312 314 316

400

402b

402a

600

ORAL COMPOSITION FOR PERIMENOPAUSE

PRIORITY CLAIM

This application claims the benefit of U.S. Provisional Patent Application No. 63/396,124 entitled "ORAL COMPOSITION FOR PERIMENOPAUSE" and filed on Aug. 12, 2022 for Marina Pene, et al., which is incorporated herein by reference in its entirety for all purposes.

FIELD OF THE INVENTION

This invention relates to compositions and more particularly relates to oral compositions to address symptoms of perimenopause.

BACKGROUND

There are at least 34 symptoms of perimenopause. 75% or more of women experience perimenopausal symptoms that can diminish their quality of life. For example, some common symptoms may include anxiety, mood changes, disturbed sleep, blood sugar imbalance, fatigue, reduced digestive capacity, reduced memory, brain fog, low libido, and/or other symptoms.

BRIEF SUMMARY

Compositions are disclosed to treat one or more symptoms of perimenopause. In one embodiment, a composition includes a cannabidiol. A composition, in a further embodiment, includes a *Curcuma longa* extract. In some embodiments, a composition includes a *Lepidium meyenii* extract.

Methods of manufacturing a composition are presented. In one embodiment, a method comprises including a cannabidiol in a composition. A method, in certain embodiments, comprises including a *Curcuma longa* extract in a composition. A method, in a further embodiment, comprises including a *Lepidium meyenii* extract in a composition.

Methods of administering a composition are presented. In one embodiment, a method includes administering a cannabidiol of a composition. A method, in some embodiments, includes administering a *Curcuma longa* extract of a composition. In certain embodiments, a method includes administering a *Lepidium meyenii* extract of a composition.

BRIEF DESCRIPTION OF THE DRAWINGS

In order that the advantages of the subject matter of the present disclosure will be readily understood, a more particular description of the subject matter will be rendered by reference to specific embodiments that are illustrated in the appended drawings. Understanding that these drawings depict only typical embodiments of the subject matter of the present disclosure and are not therefore to be considered to be limiting of its scope, the subject matter will be described and explained with additional specificity and detail through the use of the accompanying drawings, in which.

DETAILED DESCRIPTION

The subject matter of the present disclosure has been developed in response to the present state of the art in oral compositions. Accordingly, the subject matter of the present disclosure has been developed to provide a composition that overcomes many or all or some shortcomings in the prior art.

Figure 1:
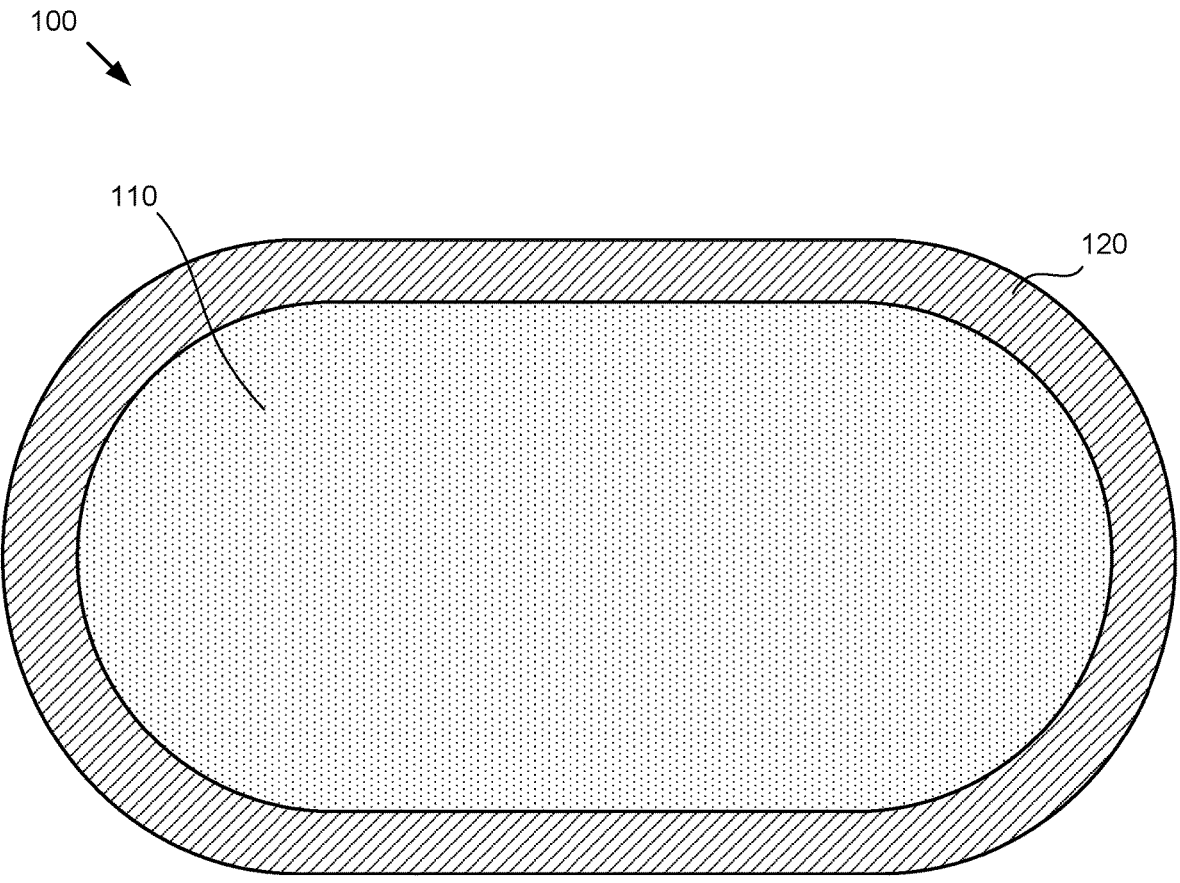
FIG. 1 is a cross-sectional view of one embodiment of a composition.

FIG. 1 depicts one embodiment of a composition 100 (e.g., an oral composition or the like) that includes a mixture 110 encapsulated within a capsule 120 and/or tablet 120. Generally, the composition 100 of the present disclosure is configured for oral ingestion. In some embodiments, the mixture 110 includes ingredients formulated to alleviate one or more symptoms of perimenopause, such as tension, anxiety, mood changes, disturbed sleep/insomnia, blood sugar imbalance, sugar cravings, fatigue, reduced digestive capacity, poor gut health, indigestion, gas, bloating, reduced memory, brain fog, lack of concentration, low libido, hot flashes, weight gain, joint pain, and/or other symptoms. Perimenopause, in certain embodiments, is a time during which a woman's body makes a natural transition to menopause, marking an end of a reproductive period for the woman.

For example, in one embodiment, the mixture 110 may include one or more ingredients selected for stress management, such as cannabidiol (CBD) (e.g., CBD isolate, CBD oil, full spectrum CBD, broad spectrum CBD, without tetrahydrocannabinol (THC), or the like), *Withania somnifera* (e.g., ashwagandha, winter cherry, or the like) extract, *Lepidium meyenii* (e.g., maca, Peruvian ginseng, or the like) extract, *Schisandra chinensis* extract, and/or another ingredient for stress management.

In a further embodiment, the mixture 110 may include one or more ingredients selected for blood sugar balance, such as *Cinnamomum verum* extract, *Curcuma longa* (e.g., turmeric, or the like) extract, and/or another ingredient for blood sugar balance. In some embodiments, the mixture 110 may include one or more ingredients selected for gut health, such as *Curcuma longa* (e.g., turmeric, or the like) extract, *Cynara scolymus* (e.g., artichoke, or the like), and/or another ingredient for gut health. The mixture 110, in certain embodiments, may include one or more ingredients selected for liver management, such as *Cynara scolymus* (e.g., artichoke, or the like), *Curcuma longa* (e.g., turmeric, or the like) extract, *Schisandra chinensis* extract, and/or another ingredient for liver management.

In some embodiments, the mixture 110 may include one or more ingredients selected to increase energy levels and/or reduce fatigue, such as *Lepidium meyenii* (e.g., maca, Peruvian ginseng, or the like) extract, *Schisandra chinensis* extract, and/or another ingredient to increase energy levels and/or reduce fatigue. The mixture 110, in one embodiment, may include one or more ingredients selected to improve mood and/or reduce anxiety, such as *Withania somnifera* (e.g., ashwagandha, winter cherry, or the like) extract, *Lepidium meyenii* (e.g., maca, Peruvian ginseng, or the like) extract, and/or another ingredient to improve mood and/or reduce anxiety. In certain embodiments, the mixture 110 may include one or more ingredients selected to improve libido, such as *Lepidium meyenii* (e.g., maca, Peruvian ginseng, or the like) extract, *Withania somnifera* (e.g., ashwagandha, winter cherry, or the like) extract, and/or another ingredient to improve libido. The mixture 110, in a further embodiment, may include one or more ingredients selected to improve memory and/or concentration, such as *Withania somnifera* (e.g., ashwagandha, winter cherry, or the like) extract, and/or another ingredient to improve memory and/or concentration.

In some embodiments, the mixture 110 may include one or more ingredients selected to help with poor sleep, such as cannabidiol (CBD), *Withania somnifera* (e.g., ashwagandha, winter cherry, or the like) extract, and/or another ingredient to help with poor sleep. The mixture 110, in certain embodiments, may include one or more ingredients selected to help repress sugar cravings, such as *Curcuma longa* (e.g., turmeric, or the like) extract, *Cynara scolymus* (e.g., artichoke, or the like) extract, *Cinnamomum verum* extract, and/or another ingredient to help repress sugar cravings. In one embodiment, the mixture 110 may include one or more ingredients selected to help control bloating, such as *Curcuma longa* (e.g., turmeric, or the like) extract, *Cynara scolymus* (e.g., artichoke, or the like) extract, *Cinnamomum verum* extract, *Schisandra chinensis* extract, and/or another ingredient to help control bloating.

In a further embodiment, the mixture 110 may include one or more ingredients selected to address joint pain, such as *Curcuma longa* (e.g., turmeric, or the like) extract, and/or another ingredient to address joint pain. In some embodiments, the mixture 110 may include one or more ingredients selected to address hot flashes, such as *Schisandra chinensis* extract, *Lepidium meyenii* (e.g., maca, Peruvian ginseng, or the like) extract, and/or another ingredient to address hot flashes. In certain embodiments, the mixture 110 may include one or more ingredients selected to address low immunity, such as cannabidiol (CBD), *Curcuma longa* (e.g., turmeric, or the like) extract, and/or another ingredient to address low immunity.

In various embodiments, the mixture 110 may include, among other ingredients, one or more of microcrystalline cellulose (MCC), xanthan gum, magnesium stearate, and/or other ingredients (e.g., one or more tableting excipients, powder flow agents, anti-caking agents, stabilizers, emulsifiers, bulking agents, release agents, desiccant agents, or the like).

The capsule 120 may be made from a variety of materials and may be manufactured according to various procedures. Generally, the capsule 120 is configured to dissolve in the stomach and/or digestive tract of a user after being swallowed, thus allowing the encapsulated mixture 110 to be digested and/or to enter the bloodstream of the user. In other embodiments, the composition 100 may comprise a pill, solid tablet, dissolvable tablet, chewable tablet, nasal spray, oral spray, lozenge, liquid and/or syrup suspension, sublingual tablet, cheek tablet, sprinkle capsule to be taken with food, a buccal tablet, a powdered drink mix and/or beverage, dermal patch, suppository, and/or other composition 100.

The capsule 120, according to one embodiment, may be made from a gelatinous material that is selected according to its ability to dissolve. For example, the capsule 120 may be made from gelatin that has a bovine, porcine, fish, and/or poultry origin (e.g., porcine gelatin, fish gelatin, a combination of porcine and fish gelatin, or the like). In another embodiment, the capsule 120 may be constructed from agar or other plant-based gelatinous substances. In such embodiments, an additional additive may be implemented into the capsule 120 in order to facilitate the dissolution of the capsule 120. For example, a pH modifying agent may also be incorporated into the capsule 120 to facilitate the dissolving reaction.

Figure 2:
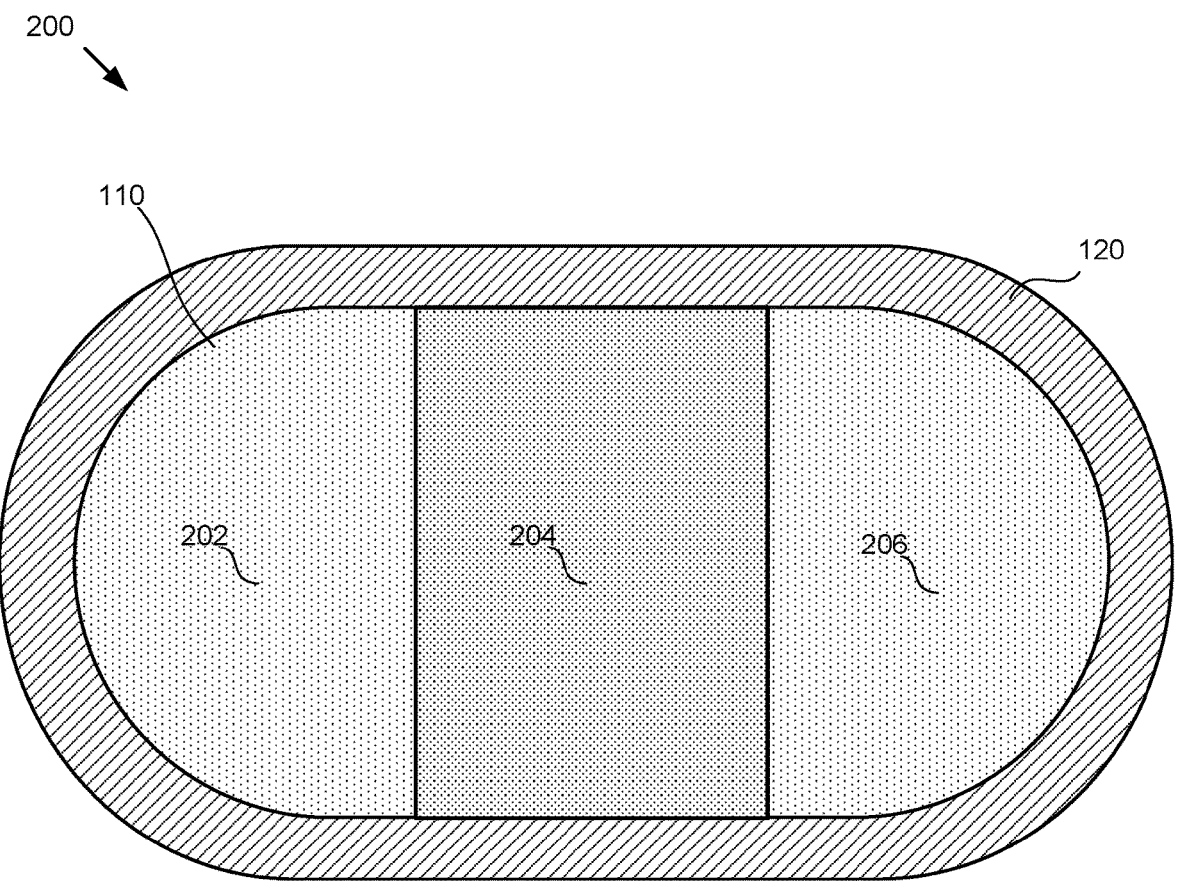
FIG. 2 is a cross-sectional view of one embodiment of a composition.

FIG. 2 depicts one embodiment of a composition 200 (e.g., an oral composition, or the like) that includes a mixture 110 encapsulated within a capsule 120 and/or tablet 120. In the depicted embodiment, the composition 200 includes at least a cannabidiol 202 (e.g., CBD isolate, CBD oil, full spectrum CBD, broad spectrum CBD, without THC, or the like), a *Curcuma longa* extract 204, a *Lepidium meyenii* extract 206, and/or other ingredients 110. While a single capsule 120 and/or tablet 120 is depicted, in certain embodiments, a dosage of the mixture 110 may comprise a single or multiple capsules 120 and/or tablets 120, such as one capsule 120 and/or tablet 120, two capsules 120 and/or tablets 120, three capsules 120 and/or tablets 120, four capsules 120 and/or tablets 120, more than four capsules 120 and/or tablets 120, one capsule 120 and/or tablet 120 in the morning and one capsule 120 and/or tablet 120 in the afternoon, evening, and/or night, two capsules 120 and/or tablets 120 in the morning and two capsules 120 and/or tablets 120 in the afternoon, evening and/or night, or another number of capsules 120 and/or tablets 120 at varying times of the day.

In one embodiment, the cannabidiol 202 comprises between about 0.1% and 5% of the composition 200, by weight. In a further embodiment, the cannabidiol 202 comprises between about 1% and 3% of the composition 200, by weight. The cannabidiol 202, in some embodiments, comprises about 2% of the composition 200, by weight. In a further embodiment, the cannabidiol 202 comprises at least about 1.5% of the composition 200, by weight. In another embodiment, the cannabidiol 202 comprises at least about 1.6% of the composition 200, by weight. In some embodiments, the cannabidiol 202 comprises at least about 1.7% of the composition 200, by weight. In a further embodiment, the cannabidiol 202 comprises at least about 1.8% of the composition 200, by weight. In one embodiment, the cannabidiol 202 comprises at least about 1.9% of the composition 200, by weight. In certain embodiments, the cannabidiol 202 comprises at least about 2% of the composition 200, by weight. In a further embodiment, the cannabidiol 202 comprises at least about 2.5% of the composition 200, by weight. In some embodiments, the cannabidiol 202 comprises at least about 3% of the composition 200, by weight.

For example, in various embodiments a dose of the composition 200 may comprise between about 5 mg and 100 mg of the cannabidiol 202, between about 10 mg and 95 mg of the cannabidiol 202, between about 15 mg and 90 mg of the cannabidiol 202, between about 20 mg and 80 mg of the cannabidiol 202, between about 25 mg and mg of the cannabidiol 202, between about 30 mg and 70 mg of the cannabidiol 202, between about 35 mg and 65 mg of the cannabidiol 202, between about 40 mg and 60 mg of the cannabidiol 202, between about 45 mg and 55 mg of the cannabidiol 202, about 5 mg of the cannabidiol 202, about 10 mg of the cannabidiol 202, about 15 mg of the cannabidiol 202, about 20 mg of the cannabidiol 202, about 25 mg of the cannabidiol 202, about 30 mg of the cannabidiol 202, about 35 mg of the cannabidiol 202, about 40 mg of the cannabidiol 202, about 45 mg of the cannabidiol 202, about 50 mg of the cannabidiol 202, about 55 mg of the cannabidiol 202, about 60 mg of the cannabidiol 202, about 65 mg of the cannabidiol 202, about 70 mg of the cannabidiol 202, about 75 mg of the cannabidiol 202, about 80 mg of the cannabidiol 202, about 85 mg of the cannabidiol 202, about 90 mg of the cannabidiol 202, about 95 mg of the cannabidiol 202, about 100 mg of the cannabidiol 202, or the like.

In some embodiments, the cannabidiol 202 comprises about 0% THC, little or no THC, or the like. The cannabidiol 202, in certain embodiments, may comprise greater than about 98% cannabidiol. In one embodiment, the cannabidiol 202 may comprise greater than about 98.5% cannabidiol. In a further embodiment, the cannabidiol 202 may comprise greater than about 99% cannabidiol. In some embodiments, the cannabidiol 202 may comprise greater than about 99.1% cannabidiol. In certain embodiments, the cannabidiol 202 may comprise greater than about 99.2% cannabidiol. In a further embodiment, the cannabidiol 202 may comprise greater than about 99.3% cannabidiol. In one embodiment, the cannabidiol 202 may comprise greater than about 99.4% cannabidiol. The cannabidiol 202, in some embodiments, may comprise greater than about 99.5% cannabidiol. In a further embodiment, the cannabidiol 202 may comprise greater than about 99.6% cannabidiol. In certain embodiments, the cannabidiol 202 may comprise greater than about 99.7% cannabidiol. In another embodiment, the cannabidiol 202 may comprise greater than about 99.8% cannabidiol.

The cannabidiol 202, in one embodiment, comprises at least about 99% cannabinoids (e.g., CBDV, CBN, CBGa, CBG, CBC, or the like). In a further embodiment, the cannabidiol 202 comprises at least about 99.5% cannabinoids. The cannabidiol 202, in some embodiments, comprises at least about 99.75% cannabinoids. In certain embodiments, the cannabidiol 202 comprises at least about 99.9% cannabinoids. In another embodiment, the cannabidiol 202 comprises at least about 99.95% cannabinoids. The cannabidiol 202, in a further embodiment, comprises at least about 99.97% cannabinoids.

In one embodiment, the *Curcuma longa* extract 204 comprises between about 15% and 55% of the composition 200, by weight. In a further embodiment, the *Curcuma longa* extract 204 comprises between about 20% and 50% of the composition 200, by weight. In some embodiments, the *Curcuma longa* extract 204 comprises between about 25% and 45% of the composition 200, by weight. In certain embodiments, the *Curcuma longa* extract 204 comprises between about 30% and 40% of the composition 200, by weight. In one embodiment, the *Curcuma longa* extract 204 comprises between about 32% and 38% of the composition 200, by weight. The *Curcuma longa* extract 204, in some embodiments, comprises about 35% of the composition 200, by weight.

For example, in various embodiments a dose of the composition 200 may comprise between about 50 mg and 1000 mg of the *Curcuma longa* extract 204, between about 100 mg and 900 mg of the *Curcuma longa* extract 204, between about 200 mg and 800 mg of the *Curcuma longa* extract 204, between about 300 mg and 700 mg of the *Curcuma longa* extract 204, about 300 mg of the *Curcuma longa* extract 204, about 350 mg of the *Curcuma longa* extract 204, about 400 mg of the *Curcuma longa* extract 204, about 450 mg of the *Curcuma longa* extract 204, about 500 mg of the *Curcuma longa* extract 204, about 550 mg of the *Curcuma longa* extract 204, about 600 mg of the *Curcuma*

*longa* extract 204, about 650 mg of the *Curcuma longa* extract 204, about 700 mg of the *Curcuma longa* extract 204, or the like.

In certain embodiments, the *Curcuma longa* extract 204 may be prepared with a dispersing agent comprising a carrier oil, or the like. For example, the *Curcuma longa* extract 204 may comprise a hydrophobic powder or other compound, which may be coated in a dispersing agent, such as one or more triglycerides, vegetable oils (e.g., corn oil, cottonseed oil, olive oil, soybean oil, coconut oil, sesame oil, peanut oil, or the like), and/or another carrier oil, which may more completely disperse the *Curcuma longa* extract 204 in the stomach and/or digestive tract of the user upon ingestion, enhancing a bioavailability of the *Curcuma longa* extract 204.

The *Lepidium meyenii* extract 206, in one embodiment, may comprise between about 5% and 20% of the composition 200, by weight. In a further embodiment, the *Lepidium meyenii* extract 206 comprises between about 10% and 15% of the composition 200, by weight. In some embodiments, the *Lepidium meyenii* extract 206 comprises between about 12% and 14% of the composition 200, by weight. The *Lepidium meyenii* extract 206, in some embodiments, comprises about 11% of the composition 200, by weight. The *Lepidium meyenii* extract 206, in one embodiment, comprises about 12% of the composition 200, by weight. The *Lepidium meyenii* extract 206, in a further embodiment, comprises about 13% of the composition 200, by weight. The *Lepidium meyenii* extract 206, in another embodiment, comprises about 14% of the composition 200, by weight. The *Lepidium meyenii* extract 206, in some embodiments, comprises about 15% of the composition 200, by weight. The *Lepidium meyenii* extract 206, in a further embodiment, comprises about 16% of the composition 200, by weight.

For example, in various embodiments a dose of the composition 200 may comprise between about 5 mg and 500 mg of the *Lepidium meyenii* extract 206, between about 100 mg and 400 mg of the *Lepidium meyenii* extract 206, between about 150 mg and 350 mg of the *Lepidium meyenii* extract 206, between about 200 mg and 300 mg of the *Lepidium meyenii* extract 206, about 100 mg of the *Lepidium meyenii* extract 206, about 150 mg of the *Lepidium meyenii* extract 206, about 175 mg of the *Lepidium meyenii* extract 206, about 200 mg of the *Lepidium meyenii* extract 206, about 225 mg of the *Lepidium meyenii* extract 206, about 250 mg of the *Lepidium meyenii* extract 206, about 275 mg of the *Lepidium meyenii* extract 206, about 300 mg of the *Lepidium meyenii* extract 206, about 325 mg of the *Lepidium meyenii* extract 206, about 350 mg of the *Lepidium meyenii* extract 206, or the like.

The *Lepidium meyenii* extract 206, in some embodiments, is standardized to comprise at least 0.7% glucosinolates, at least 0.8% glucosinolates, at least 0.9% glucosinolates, at least 1% glucosinolates, or the like. In one embodiment, the *Lepidium meyenii* extract 206 may comprise a powder dehydrated and ground from a *Lepidium meyenii* walp root, leaves, or the like.

The composition 200, in further embodiments, may include one or more of a *Withania somnifera* extract, a *Cynara scolymus* extract, a *Schisandra chinensis* extract, a *Cinnamomum verum* extract, microcrystalline cellulose, xanthan gum, magnesium stearate, and/or one or more other ingredients.

Figure 3:
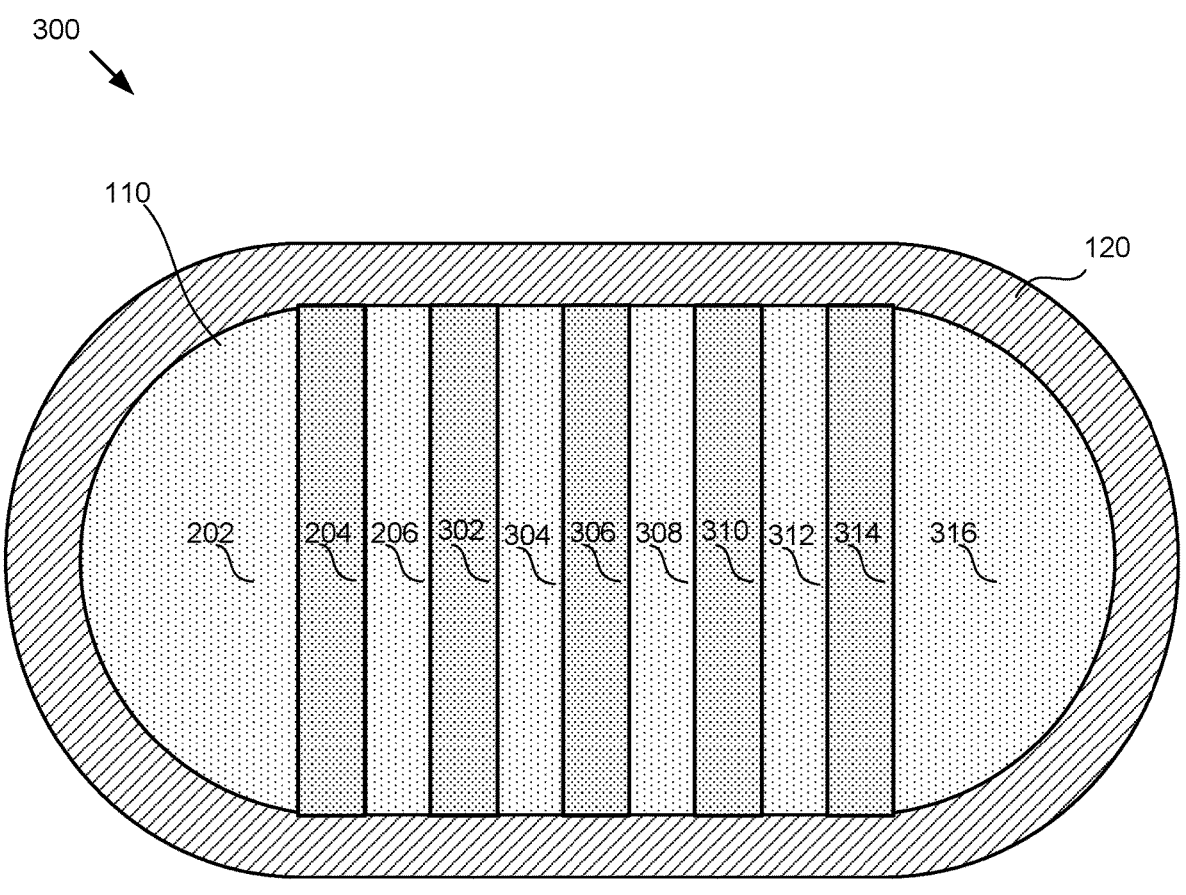
FIG. 3 is a cross-sectional view of a further embodiment of a composition.

FIG. 3 depicts one embodiment of a composition 300 (e.g., an oral composition, or the like) that includes a mixture 110 encapsulated within a capsule 120 and/or tablet 120. In the depicted embodiment, the composition 200 includes at least a cannabidiol 202, a *Curcuma longa* extract 204, a *Lepidium meyenii* extract 206, a *Withania somnifera* extract 302, a *Cynara scolymus* extract 304, a *Schisandra chinensis* extract 306, a *Cinnamomum verum* extract 308, microcrystalline cellulose 310, xanthan gum 312, magnesium stearate 314, and/or one or more other ingredients 316.

In one embodiment, the *Withania somnifera* extract 302 comprises between about 5% and 30% of the composition 300, by weight. In a further embodiment, the *Withania somnifera* extract 302 comprises between about 10% and 25% of the composition 300, by weight. In a further embodiment, the *Withania somnifera* extract 302 comprises between about 15% and 20% of the composition 300, by weight. In another embodiment, the *Withania somnifera* extract 302 comprises between about 16% and 18% of the composition 300, by weight. The *Withania somnifera* extract 302, in various embodiments, comprises about 14% of the composition 300, by weight, comprises about 15% of the composition 300, by weight, comprises about 16% of the composition 300, by weight, comprises about 17% of the composition 300, by weight, comprises about 18% of the composition 300, by weight, comprises about 19% of the composition 300, by weight, comprises about 20% of the composition 300, by weight, or the like.

For example, in various embodiments a dose of the composition 300 may comprise between about 5 mg and 500 mg of the *Withania somnifera* extract 302, between about 100 mg and 400 mg of the *Withania somnifera* extract 302, between about 150 mg and 350 mg of the *Withania somnifera* extract 302, between about 200 mg and 300 mg of the *Withania somnifera* extract 302, about 150 mg of the *Withania somnifera* extract 302, about 175 mg of the *Withania somnifera* extract 302, about 200 mg of the *Withania somnifera* extract 302, about 225 mg of the *Withania somnifera* extract 302, about 250 mg of the *Withania somnifera* extract 302, about 275 mg of the *Withania somnifera* extract 302, about 300 mg of the *Withania somnifera* extract 302, about 325 mg of the *Withania somnifera* extract 302, about 350 mg of the *Withania somnifera* extract 302, or the like. The *Withania somnifera* extract 302, in some embodiments, may comprise a *Withania somnifera* root extract powder 302, *Withania somnifera* fruit extract 302, *Withania somnifera* leaf extract 302, or the like.

In one embodiment, the *Cynara scolymus* extract 304 comprises between about 1% and 30% of the composition 300, by weight. In a further embodiment, the *Cynara scolymus* extract 304 comprises between about 5% and 20% of the composition 300, by weight. The *Cynara scolymus* extract 304, in some embodiments, comprises between about 8% and 15% of the composition 300, by weight. In certain embodiments. the *Cynara scolymus* extract 304 comprises between about 9% and 12% of the composition 300, by weight. The *Cynara scolymus* extract 304, in some embodiments, comprises about 5% of the composition 300, by weight. The *Cynara scolymus* extract 304, in one embodiment, comprises about 10% of the composition 300, by weight. The *Cynara scolymus* extract 304, in certain embodiments, comprises about 15% of the composition 300, by weight. The *Cynara scolymus* extract 304, in a further embodiment, comprises about 20% of the composition 300, by weight. The *Cynara scolymus* extract 304, in another embodiment, comprises about 25% of the composition 300, by weight.

For example, in various embodiments a dose of the composition 300 may comprise between about 5 mg and 500 mg of the *Cynara scolymus* extract 304, between about 50 mg and 400 mg of extract 304, between about 100 mg and 300 mg of the *Cynara scolymus* extract 304, between about 150 mg and 250 mg of the *Cynara scolymus* extract 304, about 50 mg of the *Cynara scolymus* extract 304, about 100 mg of the *Cynara scolymus* extract 304, about 150 mg of the *Cynara scolymus* extract 304, about 200 mg of the *Cynara scolymus* extract 304, about 250 mg of the *Cynara scolymus* extract 304, about 300 mg of the *Cynara scolymus* extract 304, about 350 mg of the *Cynara scolymus* extract 304, about 400 mg of the *Cynara scolymus* extract 304, or the like.

The *Cynara scolymus* extract 304, in some embodiments, may be standardized to comprise at least 3% cynarin, at least 3.5% cynarin, at least 4% cynarin, at least 5% cynarin, or the like. For example, in certain embodiments, the *Cynara scolymus* extract 304 may comprise a powder or a pulp derived from leaves of *Cynara scolymus* linn plants, or in some cases the extract 304 may comprise a powder or a pulp derived from the stems of *Cynara scolymus* linn plants, may have a maltodextrin carrier, or the like.

The *Schisandra chinensis* extract 306, in one embodiment, comprises between about 1% and 20% of the composition 300, by weight. In a further embodiment, the *Schisandra chinensis* extract 306 comprises between about 2% and 15% of the composition 300. The *Schisandra chinensis* extract 306, in some embodiments, comprises between about 3% and 10% of the composition 300 by weight. The *Schisandra chinensis* extract 306, in various embodiments, comprises about 1% of the composition 300, comprises about 2% of the composition 300, comprises about 3% of the composition 300, comprises about 4% of the composition 300, comprises about 5% of the composition 300, comprises about 6% of the composition 300, comprises about 7% of the composition 300, comprises about 8% of the composition 300, by weight, or the like.

For example, in various embodiments a dose of the composition 300 may comprise between about 1 mg and 120 mg of the *Schisandra chinensis* extract 306, between about 10 mg and 110 mg of the *Schisandra chinensis* extract 306, between about 20 mg and 100 mg of the *Schisandra chinensis* extract 306, between about 30 mg and 90 mg of the *Schisandra chinensis* extract 306, between about 40 mg and 80 mg of the *Schisandra chinensis* extract 306, between about 50 mg and 70 mg of the *Schisandra chinensis* extract 306, about 10 mg of the *Schisandra chinensis* extract 306, about 20 mg of the *Schisandra chinensis* extract 306, about 30 mg of the *Schisandra chinensis* extract 306, about 40 mg of the *Schisandra chinensis* extract 306, about 50 mg of the *Schisandra chinensis* extract 306, about 60 mg of the *Schisandra chinensis* extract 306, about 70 mg of the *Schisandra chinensis* extract 306, about 80 mg of the *Schisandra chinensis* extract 306, about 90 mg of the *Schisandra chinensis* extract 306, or the like. In one embodiment, the *Schisandra chinensis* extract 306 comprises a *Schisandra chinensis* fruit powder 306, or the like.

The *Cinnamomum verum* extract 308, in some embodiments, comprises between about 1% and 7% of the composition 300, by weight. In a further embodiment, the *Cinnamomum verum* extract 308 comprises between about 2% and 6% of the composition 300. The *Cinnamomum verum* extract 308, in one embodiment, comprises between about 3% and 5% of the composition 300, by weight. The *Cinnamomum verum* extract 308, in various embodiments, comprises about 1% of the composition 300, comprises about 2% of the composition 300, comprises about 3% of the composition 300, comprises about 4% of the composition 300, comprises about 5% of the composition 300, comprises about 6% of the composition 300, comprises about 7% of the composition 300, comprises about 8% of the composition 300, by weight, or the like.

For example, in various embodiments, a dose of the composition 300 may comprise between about 5 mg and 120 mg of the *Cinnamomum verum* extract 308, between about 20 mg and 100 mg of the *Cinnamomum verum* extract 308, between about 30 mg and mg of the *Cinnamomum verum* extract 308, between about 40 mg and 80 mg of the *Cinnamomum verum* extract 308, between about 50 mg and 70 mg of the *Cinnamomum verum* extract 308, about 10 mg of the *Cinnamomum verum* extract 308, about 20 mg of the *Cinnamomum verum* extract 308, about 30 mg of the *Cinnamomum verum* extract 308, about 40 mg of the *Cinnamomum verum* extract 308, about 50 mg of the *Cinnamomum verum* extract 308, about 60 mg of the *Cinnamomum verum* extract 308, about 70 mg of the *Cinnamomum verum* extract 308, about 80 mg of the *Cinnamomum verum* extract 308, about 90 mg of the *Cinnamomum verum* extract 308 or the like. The *Cinnamomum verum* extract 308, in one embodiment, may comprise a *Cinnamomum verum* bark powder 308, or the like.

The microcrystalline cellulose 310, in some embodiments, comprises between about 0.1% and 4% of the composition 300, by weight. In a further embodiment, the microcrystalline cellulose 310 comprises between about 1% and 3% of the composition 300, by weight. The microcrystalline cellulose 310, in various embodiments, comprises about 0.5% of the composition 300, comprises about 1% of the composition 300, comprises about 1.5% of the composition 300, comprises about 2% of the composition 300, comprises about 2.5% of the composition 300, comprises about 3% of the composition 300, comprises about 3.5% of the composition 300, by weight, or the like.

For example, in various embodiments, a dose of the composition 300 may comprise between about 5 mg and 60 mg of the microcrystalline cellulose 310, between about 10 mg and 50 mg of the microcrystalline cellulose 310, between about 20 mg and 40 mg of the microcrystalline cellulose 310, between about 25 mg and 35 mg of the microcrystalline cellulose 310, about 5 mg of the microcrystalline cellulose 310, about 10 mg of the microcrystalline cellulose 310, about 15 mg of the microcrystalline cellulose 310, about 20 mg of the microcrystalline cellulose 310, about 25 mg of the microcrystalline cellulose 310, about 30 mg of the microcrystalline cellulose 310, about 35 mg of the microcrystalline cellulose 310, about 40 mg of the microcrystalline cellulose 310, about 45 mg of the microcrystalline cellulose 310, about 50 mg of the microcrystalline cellulose 310, about 55 mg of the microcrystalline cellulose 310, about 60 mg of the microcrystalline cellulose 310, or the like.

The xanthan gum 312, in certain embodiments, may comprise between about 0.1% and 3% of the composition 300, by weight. In a further embodiment, the xanthan gum 312 comprises between about 1% and 2% of the composition 300, by weight. The xanthan gum 312, in some embodiments, comprises about 1.5% of the composition 300, by weight.

For example, in various embodiments, a dose of the composition 300 may comprise between about 5 mg and 60 mg of the xanthan gum 312, between about 10 mg and 50 mg of the xanthan gum 312, between about 20 mg and 40 mg of the xanthan gum 312, about 20 mg of the xanthan gum 312, about 25 mg of the xanthan gum 312, about 30 mg of the xanthan gum 312, about 35 mg of the xanthan gum 312, about 40 mg of the xanthan gum 312, or the like.

The magnesium stearate 314, in one embodiment, may comprise between about 0.01% and 2% of the composition 300, by weight. In a further embodiment, the magnesium stearate 314 comprises between about 0.3% and 1.8% of the composition 300, by weight. the magnesium stearate 314, in some embodiments, comprises between about 0.5% and 1.6% of the composition 300, by weight. In certain embodiments, the magnesium stearate 314 comprises between about 0.7% and 1.4% of the composition 300, by weight. The magnesium stearate 314, in another embodiment, comprises between about 0.9% and 1.2% of the composition 300, by weight. The magnesium stearate 314, in various embodiments, comprises about 0.75% of the composition 300, comprises about of the composition 300, comprises about 0.85% of the composition 300, comprises about 0.9% of the composition 300, comprises about 0.95% of the composition 300, comprises about 1% of the composition 300, comprises about 1.05% of the composition 300, comprises about 1.1% of the composition 300, comprises about 1.15% of the composition 300, comprises about 1.2% of the composition 300, comprises about 1.25% of the composition 300, by weight, or the like.

For example, in various embodiments, a dose of the composition 300 may comprise between about 1 mg and 30 mg of the magnesium stearate 314, between about 5 mg and 25 mg of the magnesium stearate 314, between about 10 mg and 20 mg of the magnesium stearate 314, about 5 mg of the magnesium stearate 314, about 10 mg of the magnesium stearate 314, about 15 mg of the magnesium stearate 314, about 20 mg of the magnesium stearate 314, about 25 mg of the magnesium stearate 314, or the like.

Figure 4:
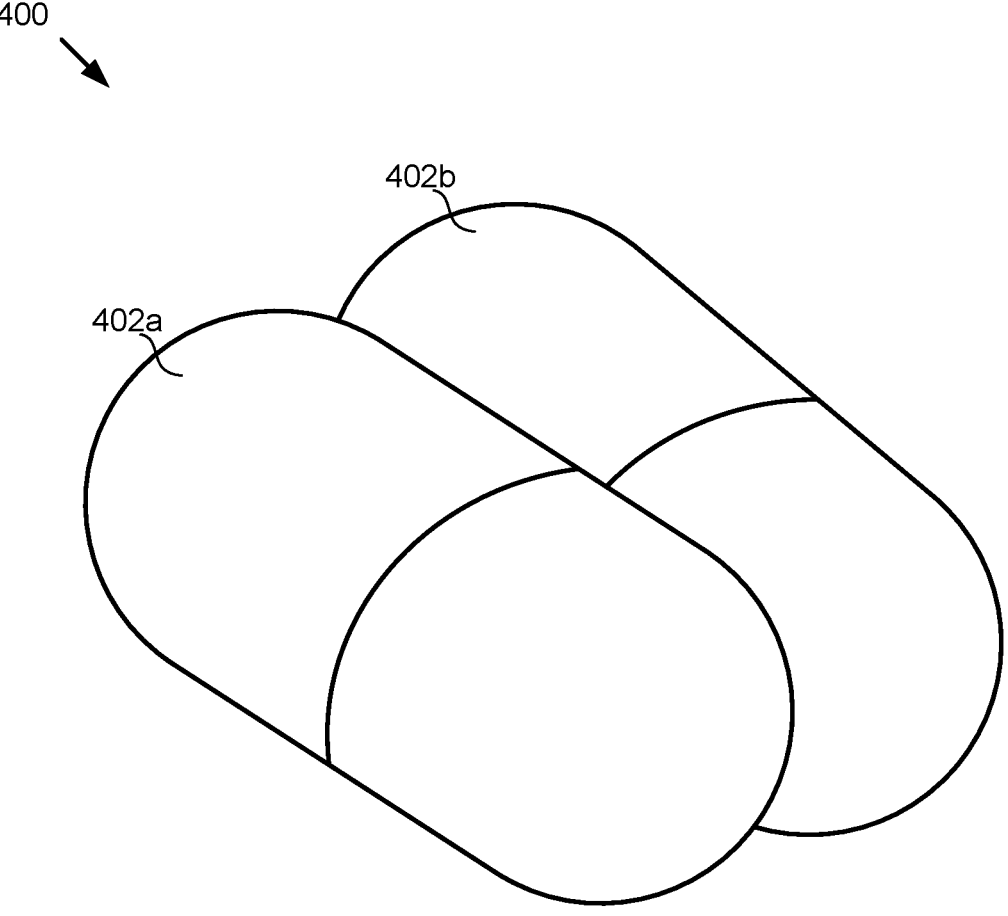
FIG. 4 is a perspective view of one embodiment of a composition.

FIG. 4 depicts one embodiment of a composition 400 (e.g., an oral composition, or the like). In the depicted embodiment, the composition 400 comprises a plurality of capsules 402a-b and/or tablets 402a-b. While two capsules 402a-b and/or tablets 402a-b are depicted, in certain embodiments, a dosage of the composition 400 may comprise a single capsules 402 and/or tablet 402, three capsules 402a-b and/or tablets 402a-b, four capsules 402a-b and/or tablets 402a-b, more than four capsules 402a-b and/or tablets 402a-b, two capsules 402a-b and/or tablets 402a-b in the morning and two capsules 402a-b and/or tablets 402a-b in the afternoon or evening, or another number of capsules 402a-b and/or tablets 402a-b, a liquid suspension, a powdered drink mix, and/or other composition 400.

Figure 5A:
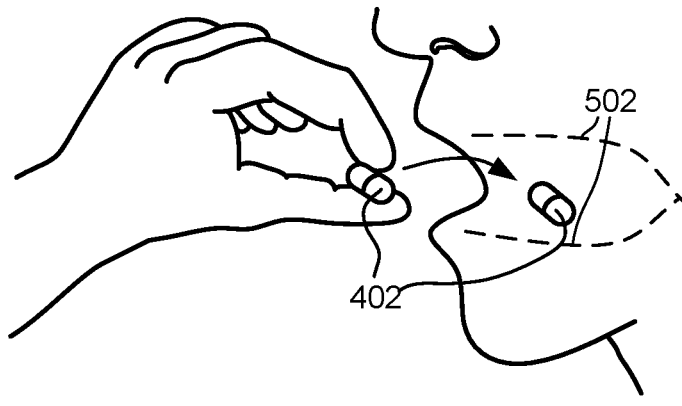
FIG. 5A depicts one embodiment of a user ingesting a composition.

FIG. 5A depicts one embodiment of a user ingesting an oral composition 402. In the depicted embodiment, the user has placed a first capsule 402 and/or tablet 402 in the user's mouth 502 and is in the process of placing a second capsule 402 and/or tablet 402 in the user's mouth 502. Two capsules 402 and/or tablets 402 may comprise a single dosage, half of a dosage, a third of a dosage, a quarter of a dosage, or the like.

Figure 5B:
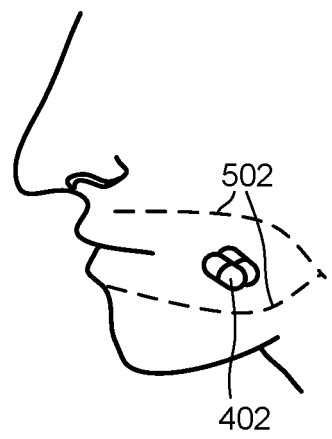
FIG. 5B depicts a further embodiment of a user ingesting a composition.

FIG. 5B depicts a further embodiment of a user ingesting an oral composition 402. In the depicted embodiment, the user has placed two capsules 402 and/or tablets 402 in the user's mouth 502, and is in the process of swallowing the capsules 402 and/or tablets 402 into the stomach and/or digestive tract of the user for digestion and absorption into the user's bloodstream, or the like.

Figure 6:
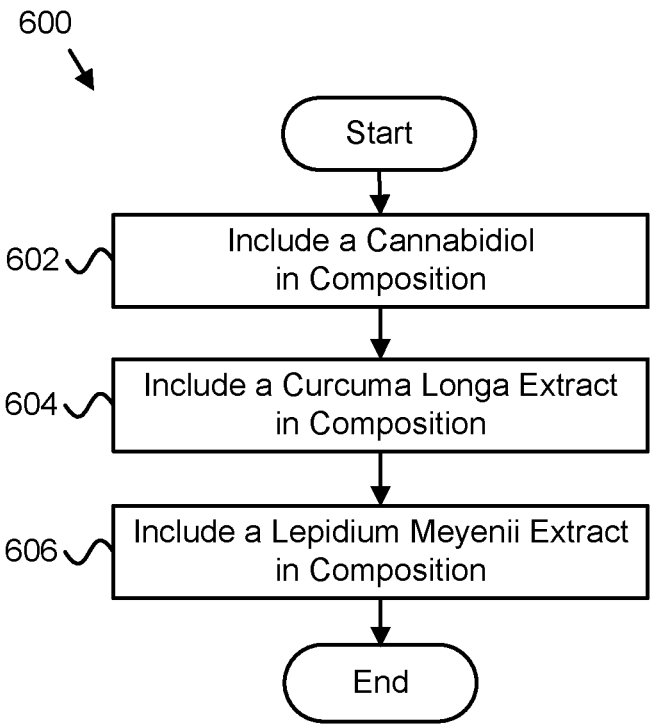
FIG. 6 is a schematic flow chart diagram illustrating one embodiment of a method of manufacturing a composition.

FIG. 6 depicts one embodiment of a method 600 of manufacturing a composition. The method 600 begins and a manufacturer includes 602 a cannabidiol in a composition. A manufacturer includes 604 a *Curcuma longa* extract in a composition. A manufacturer includes 606 a *Lepidium meyenii* extract in a composition and the method 600 ends.

Figure 7:
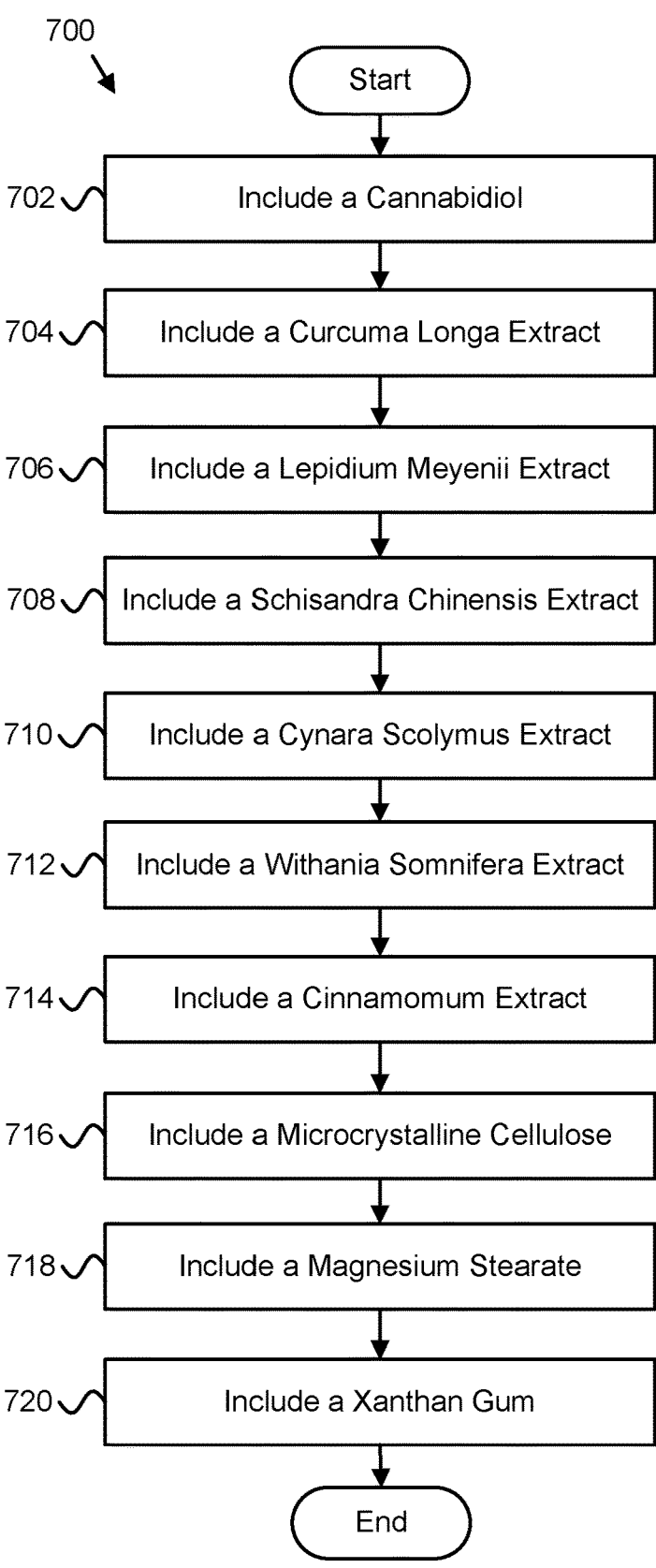
FIG. 7 is a schematic flow chart diagram illustrating a further embodiment of a method of manufacturing a composition.

FIG. 7 depicts one embodiment of a method 700 of manufacturing a composition. The method 700 begins and a manufacturer includes 702 a cannabidiol in a composition. A manufacturer includes 704 a *Curcuma longa* extract in a composition. A manufacturer includes 706 a *Lepidium meyenii* extract in a composition.

A manufacturer includes 708 a *Schisandra chinensis* extract in a composition. A manufacturer includes 710 a *Cynara scolymus* extract in a composition. A manufacturer includes 712 a *Withania somnifera* extract in a composition. A manufacturer includes 714 a *Cinnamomum verum* extract in a composition.

A manufacturer includes 716 a microcrystalline cellulose in a composition. A manufacturer includes 718 a magnesium stearate in a composition. A manufacturer includes 720 a xanthan gum in a composition and the method 700 ends.

Figure 8:
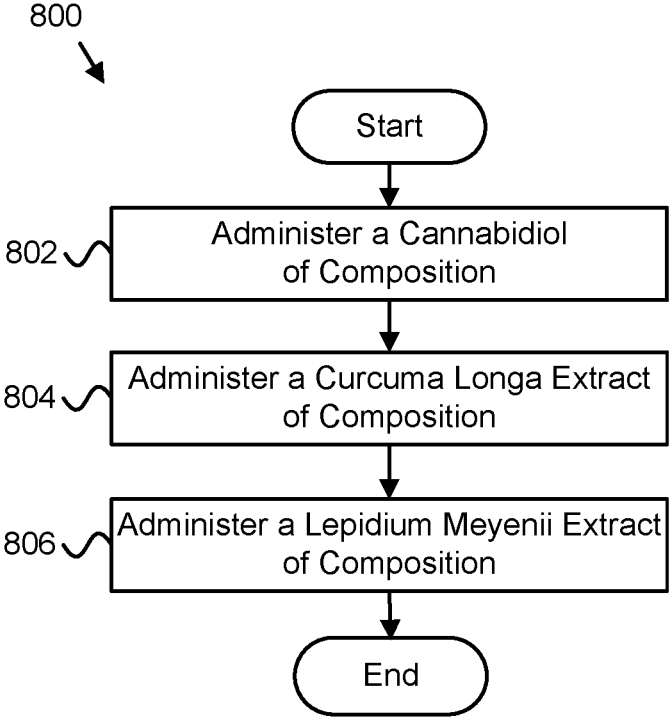
FIG. 8 is a schematic flow chart diagram illustrating one embodiment of a method for administering a composition.

FIG. 8 depicts one embodiment of a method 800 of administering a composition. The method 800 begins and a user administers 802 a cannabidiol of a composition. A user administers 804 a *Curcuma longa* extract of a composition. A user administers 806 a *Lepidium meyenii* extract of a composition and the method 800 ends.

Figure 9:
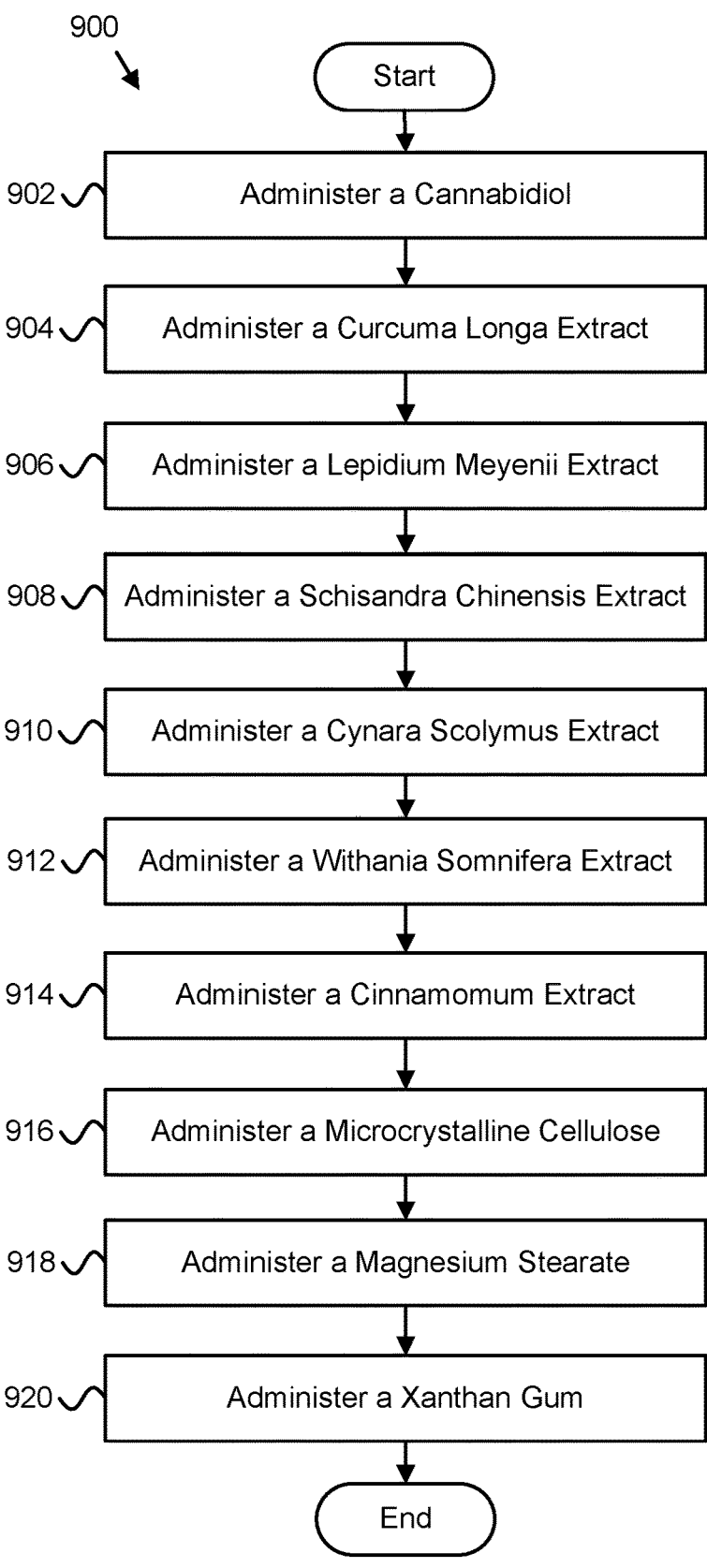
FIG. 9 is a schematic flow chart diagram illustrating a further embodiment of a method for administering a composition.

FIG. 9 depicts one embodiment of a method 900 of administering a composition. The method 900 begins and a user administers 902 a cannabidiol of a composition. A user administers 904 a *Curcuma longa* extract of a composition. A user administers 906 a *Lepidium meyenii* extract of a composition.

A user administers 908 a *Schisandra chinensis* extract of a composition. A user administers 910 a *Cynara scolymus* extract of a composition. A user administers 912 a *Withania somnifera* extract of a composition. A user administers 914 a *Cinnamomum verum* extract of a composition.

A user administers 916 a microcrystalline cellulose of a composition. A user administers 918 a magnesium stearate of a composition. A user administers 920 a xanthan gum of a composition and the method 900 ends.

Reference throughout this specification to features, advantages, or similar language does not imply that all of the features and advantages that may be realized with the subject matter of the present disclosure should be or are in any single embodiment of the subject matter. Rather, language referring to the features and advantages is understood to mean that a specific feature, advantage, or characteristic described in connection with an embodiment is included in at least one embodiment of the subject matter of the present disclosure. Thus, discussion of the features and advantages, and similar language, throughout this specification may, but do not necessarily, refer to the same embodiment.

Furthermore, the described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

Similarly, reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the subject matter of the present disclosure, however, absent an express correlation to indicate otherwise, an implementation may be associated with one or more embodiments.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A composition comprising:

one or more of a capsule, a tablet, a lozenge, and a powdered drink mix configured to dissolve in the digestive tract of a user and for alleviating one or more symptoms of perimenopause including one or more of anxiety, mood changes, disturbed sleep, blood sugar imbalance, fatigue, reduced digestive capacity, reduced memory, brain fog, low libido, hot flashes, and joint pain, comprising:

a cannabidiol comprising between about 0.1% and 5% of the composition, by weight;

a *Curcuma longa* extract prepared with a dispersing agent comprising a carrier oil, wherein the *Curcuma longa* extract comprises between about 15% and 55% of the composition, by weight;

a *Lepidium meyenii* extract standardized to comprise at least 0.7% glucosinolates, wherein the *Lepidium meyenii* extract comprises between about 5% and 20% of the composition, by weight;

a *Withania somnifera* extract comprising between about 5% and 30% of the composition, by weight;

a *Cynara scolymus* extract standardized to comprise at least 3% cynarin, wherein the *Cynara scolymus* extract comprises between about 1% and 30% of the composition, by weight:

a *Schisandra chinensis* extract comprising between about 1% and 20% of the composition, by weight; and a *Cinnamomum verum* extract comprising between about 1% and 7% of the composition, by weight.

2. The composition of claim 1, wherein the *Schisandra chinensis* extract comprises a *Schisandra chinensis* fruit powder.

3. The composition of claim 2, wherein the *Schisandra chinensis* extract comprises between 1% and 10% of the composition, by weight.

4. The composition of claim 1, wherein the *Cynara scolymus* extract comprises between 1% and 20% of the composition, by weight.

5. The composition of claim 1, wherein the *Withania somnifera* extract comprises between 10% and 30% of the composition, by weight.

6. The composition of claim 5, wherein the *Withania somnifera* extract comprises a *Withania somnifera* root extract powder.

7. The composition of claim 1, wherein the *Lepidium meyenii* extract comprises between 10% and 20% of the composition, by weight.

8. The composition of claim 1, wherein the *Cinnamomum verum* extract comprises a *Cinnamomum verum* bark powder.

9. The composition of claim 1, further comprising microcrystalline cellulose, wherein the microcrystalline cellulose comprises between 0.1% and 3% of the composition, by weight.

10. The composition of claim 1, further comprising xanthan gum, wherein the xanthan gum comprises between 0.1% and 3% of the composition, by weight.

11. The composition of claim 1, further comprising magnesium stearate, wherein the magnesium stearate comprises between 0.01% and 2% of the composition, by weight.

12. A method of manufacturing a composition, the method comprising:

manufacturing a composition comprising one or more of a capsule, a tablet, a lozenge, and a powdered drink mix configured to dissolve in the digestive tract of a user and for alleviating one or more symptoms of perimenopause including one or more of anxiety, mood changes, disturbed sleep, blood sugar imbalance, fatigue, reduced digestive capacity, reduced memory, brain fog, low libido, hot flashes, and joint pain, the composition further comprising:

a cannabidiol comprising between about 0.1% and 5% of the composition, by weight;

a *Curcuma longa* extract prepared with a dispersing agent comprising a carrier oil, wherein the *Curcuma longa* extract comprises between about 15% and 55% of the composition, by weight;

a *Lepidium meyenii* extract standardized to comprise at least 0.7% glucosinolates, wherein the *Lepidium meyenii* extract comprises between about 5% and 20% of the composition, by weight;

a *Withania somnifera* extract comprising between about 5% and 30% of the composition, by weight:

a *Cynara scolymus* extract standardized to comprise at least 3% cynarin, wherein the *Cynara scolymus* extract comprises between about 1% and 30% of the composition, by weight;

a *Schisandra chinensis* extract comprising between about 1% and 20% of the composition, by weight; and a *Cinnamomum verum* extract comprising between about 1% and 7% of the composition, by weight.

13. A method of administering a composition, the method comprising:

administering a composition comprising one or more of a capsule, a tablet, a lozenge, and a powdered drink mix configured to dissolve in the digestive tract of a user and for alleviating one or more symptoms of perimenopause including one or more of anxiety, mood changes, disturbed sleep, blood sugar imbalance, fatigue, reduced digestive capacity, reduced memory, brain fog, low libido, hot flashes, and joint pain, the composition further comprising:

a cannabidiol comprising between about 0.1% and 5% of the composition, by weight;

a *Curcuma longa* extract prepared with a dispersing agent comprising a carrier oil, wherein the *Curcuma longa* extract comprises between about 15% and 55% of the composition, by weight;

a *Lepidium meyenii* extract standardized to comprise at least 0.7% glucosinolates, wherein the *Lepidium meyenii* extract comprises between about 5% and 20% of the composition, by weight:

a *Withania somnifera* extract comprising between about 5% and 30% of the composition, by weight;

a *Cynara scolymus* extract standardized to comprise at least 3% cynarin, wherein the *Cynara scolymus* extract comprises between about 1% and 30% of the composition, by weight;

a *Schisandra chinensis* extract comprising between about 1% and 20% of the composition, by weight; and a *Cinnamomum verum* extract comprising between about 1% and 7% of the composition, by weight.

* * * * *